United States Patent [19]

Jobe

[11] Patent Number: 4,643,724
[45] Date of Patent: Feb. 17, 1987

[54] SYRINGE HOLDER

[75] Inventor: Michael J. Jobe, Fort Worth, Tex.

[73] Assignee: Alcon Laboratories, Inc., Fort Worth, Tex.

[21] Appl. No.: 809,668

[22] Filed: Dec. 16, 1985

[51] Int. Cl.⁴ .......................................... A61M 5/245
[52] U.S. Cl. .................................................... 604/232
[58] Field of Search ............... 604/240, 241, 187, 232, 604/224

[56] References Cited

U.S. PATENT DOCUMENTS

| | | | |
|---|---|---|---|
| 3,076,455 | 2/1963 | McConnaughey et al. | 604/232 |
| 3,596,659 | 8/1971 | Glasser . | |
| 3,848,593 | 11/1974 | Baldwin | 604/232 |
| 3,964,139 | 6/1976 | Kleinmann et al. | 24/254 |
| 3,993,064 | 11/1976 | McCarthy et al. | 604/224 |
| 4,062,353 | 12/1977 | Foster et al. | 604/187 |
| 4,122,836 | 10/1978 | Burnett | 128/1.1 |
| 4,452,473 | 6/1984 | Ruschke | 285/81 |
| 4,540,405 | 9/1985 | Miller et al. | 604/241 |

Primary Examiner—John D. Yasko
Attorney, Agent, or Firm—James A. Arno; Gregg C. Brown

[57] ABSTRACT

A syringe holder for receiving a syringe and provided with a locking device to lock the needle assembly onto the syringe to prevent the needle assembly from dislodging during administration or loading of a viscous material. The holder is also provided with grips for control of the syringe during use.

9 Claims, 9 Drawing Figures

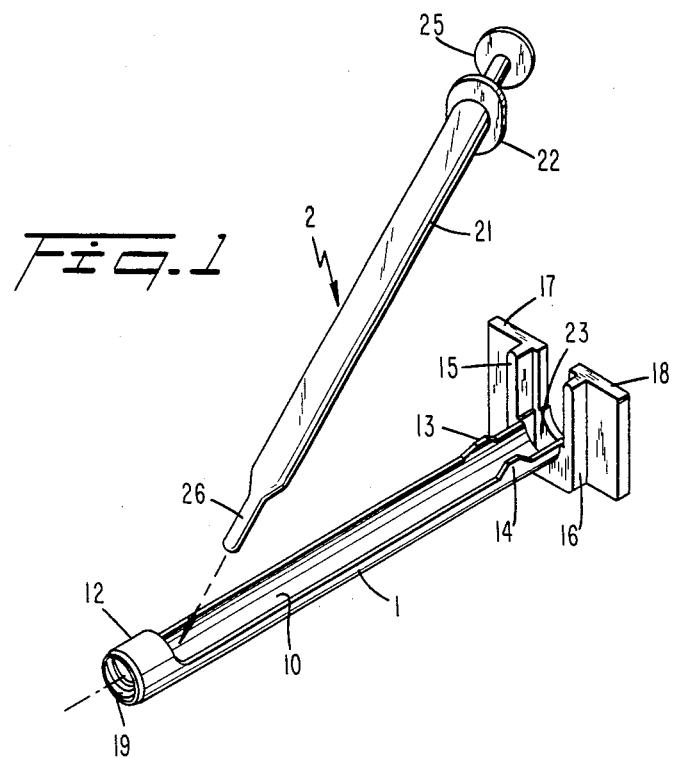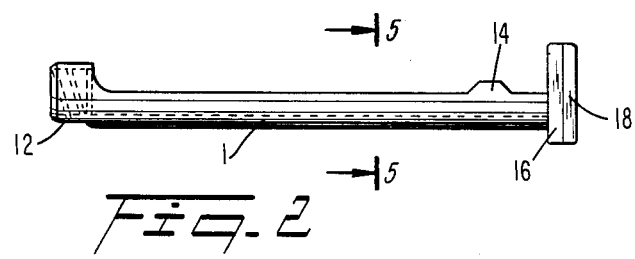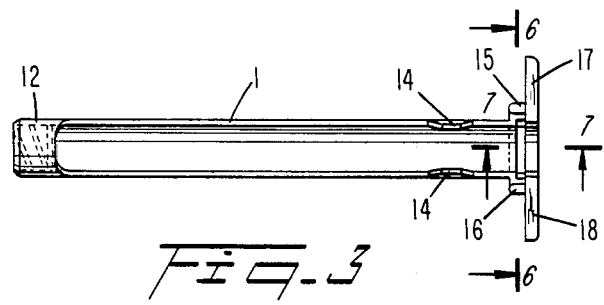

SYRINGE HOLDER

BACKGROUND OF THE INVENTION

1. Field of the Invention

The present invention relates to a syringe holder and, more particularly, to holding means for syringes which are not provided with a locking device for needles.

2. Discussion of Related Art

Many of the syringes currently being marketed are not provided with means for locking or securing the needle and needle holder (hereinafter referred to as the "needle assembly") to the front of the syringe barrel. This lack of securing or locking means is particularly prevalent among disposable syringes. The lack of a means for securing the needle assembly to the barrel of the syringe creates a difficult and troublesome problem when the syringe is utilized to administer a viscous substance. Namely, the needle assembly is simply blown off the front of the syringe by the hydraulic pressure created when the plunger and piston of the syringe are advanced to force the viscous substance through the needle.

Although the prior art discloses holders for syringes serving various purposes, these holders either fail to address the abovediscussed problem or fail to completely resolve the problem. For example, U.S. Pat. Nos. 3,596,659 to Glasser and 4,122,836 to Burnett both teach syringe holders which have a shielding effect from some sort of radiation or particle bombardment. These patents are concerned with shielding the barrel of the syringe and are not concerned with the problem of connecting a noncompatible needle with the barrel of the syringe.

U.S. Pat. No. 3,964,139 to Kleinmann et al., teaches a syringe holder, but again, the focus is not on holding the syringe to enable two otherwise noncompatible parts to brought together. Rather, the syringe holder is useful in an infusion pump (column 1, lines 2-3).

The use of a luer connection system to provide a secure, fluid type connection is also known in the art. For example, U.S. Pat. No. 4,452,473 to Ruschke teaches a luer connection system. However, this patent is concerned with the connecting aspect of the Ruschke invention and has no disclosure relating to the use of a luer connection system in a syringe holder.

Applicant has recently become aware of another type of syringe holder currently available; this syringe holder is illustrated in FIG. 9 of the accompanying drawings. This syringe holder includes a luer connection system designed to prevent the needle assembly from being blown off the syringe barrel. However, the syringe holder is not provided with means for positively preventing the syringe from being pulled free of the needle assembly when a viscous substance is drawn into the syringe by pulling the plunger backward, as discussed in greater detail below. Thus, this type of syringe holder only partially resolves the above-discussed problems experienced in the prior art.

SUMMARY OF THE INVENTION

It is an object of this invention to provide a syringe holder with a threaded luer lock that accepts certain syringes which are not provided with needle securing means.

It is a further object of this invention to provide a luer lock which forms a secure, fluid tight connection which prevents the hydraulic forces associated with movement of viscous liquids in the syringe from detaching the needle assembly from the syringe.

It is a still further object of this invention to provide a holder which provides both a positive lock of a needle assembly to a syringe and a positive lock of the syringe to the holder.

Other objects and advantages of the invention will become apparent as the description thereof proceeds.

In satisfaction of the foregoing objects, the present invention provides a plastic holder with a threaded locking feature at one end and means for securing the syringe to the holder at the other end thereof.

BRIEF DESCRIPTION OF THE DRAWINGS

Reference is now made to the drawing accompanying the application wherein:

FIG. 1 is a perspective illustration of a syringe and holder constructed in accordance with the principles of the present invention;

FIG. 2 is a side view of the holder;

FIG. 3 is a top view of the holder;

DESCRIPTION OF PREFERRED EMBODIMENTS

The present provides a device for securing a syringe to a needle assembly comprising a body for receiving said syringe with a front and distal end, said front end having a means for securing an ear or flange portion of said syringe to prevent axial movement between said syringe and said body, said distal end having an opening with a luer lok mechanism through which the front end of said syringe passes and whereby the luer lok secures the front of the syringe and the needle assembly.

Figure 5:
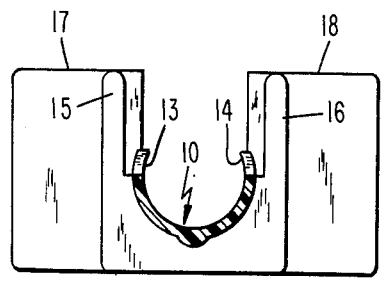
FIG. 5 is a plan cross-sectional view of the channel taken along line 5—5 of FIG. 2.

FIG. 1 represents a perspective view of the syringe holder and syringe means of the present invention. As can be seen from the drawing, the body of the holder 1 is an elongate semicircular pocket or holder which is formed to receive the circular barrel 21 of a syringe inserted into the pocket or channel 10. FIG. 5 is a plan cross sectional view taken along line 5—5 of FIG. 2 where a cross section of the elongate channel 10 is shown. The supports 15 and 16, and flanges 17 and 18 can be seen at the frontal end by this view.

Figure 4:
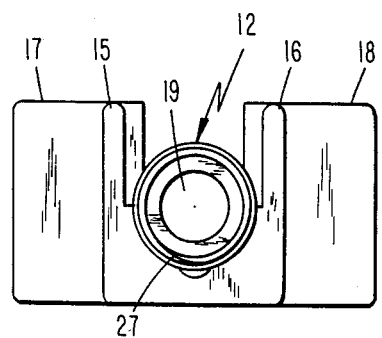
FIG. 4 is a plan cross-sectional view of a luer connection system used in accordance with the principles of the present invention.
Figure 8:
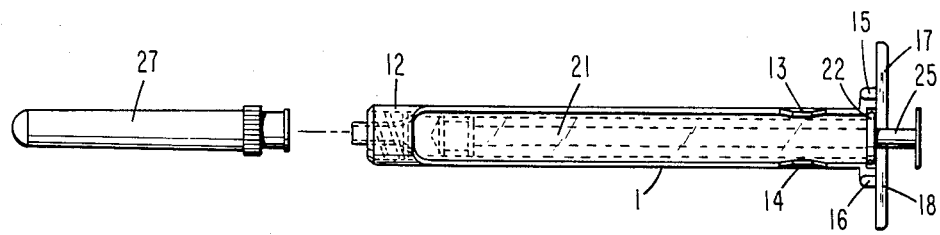
FIG. 8 is a phantom view of a syringe locked into place by the holder defined in the invention.

At the distal end of this semicircular pocket or channel can be found the threaded luer lok mechanism 12 of the present invention. The luer lok comprises a circular end portion 12 which carries threads 27 as shown in FIG. 4. The end portion 12 terminates in open end 19. This threaded design permits a needle to be locked into the tip 26 of the syringe when placed in the holder as seen in FIG. 8 where needle guard 27 is shown covering the needle. FIG. 4 represents a plan cross-sectional view along the same line as 5—5, but starting at the distal end and looking through the luer lok.

At the opposite, frontal end of the semicircular channel can be found support means or members 15 and 16 which serve as means for securing the male flange 22 of a syringe into a female receptor 23 and to provide a large finger grip for controlling the syringe.

The support means comprises flanges 17 and 18 which extend both upwardly and outwardly from the termination of semicircular pocket ends. These flanges are not directly in contact with the end of the semicircular pocket, but rather, supports 15 and 16 extend upwardly from a point immediately on either side of the semicircular channel. The supports 15, 16 have sufficient thickness between the end of the semicircular channel and the beginning of the flanges to define a recess 23 whereby a flange 22 of a syringe may be received snugly into the recess. This can be clearly seen along line 7—7 of FIG. 3 where the width of support 15 also defines the width of mating recess 23 before flange 17 commences. Line 6—6 of FIG. 3 shows the outwardly extending flanges 17 and 18 extending from supports 15 and 16. Further, both the supports and the flanges define a U-shaped recess 24 between them so that the head of the syringe 25 can fit between them just as the barrel 21 fits in the semicircular channel 10 of the body 1.

Figure 6:
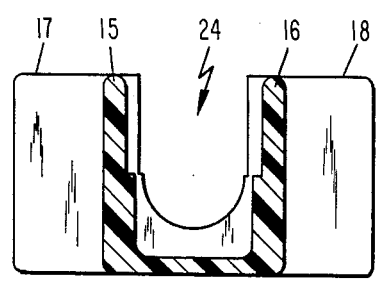
FIG. 6 is a plan sectional view of the frontal mating member and large finger holder taken along line 6—6 of FIG. 3.
Figure 7:
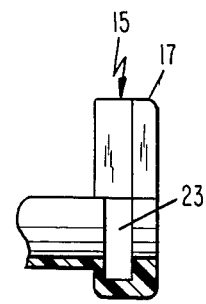
FIG. 7 is a side cross section defining the recessed mating member, support and flange taken along line 7—7 of FIG. 3.

FIG. 8 is a phantom view of a syringe in the holder with the body of the syringe 21 in the channel 10, the flange of the syringe 22 mating in the recess defined by 23 of FIG. 1 and the head of the syringe 25 mating in the U-shaped recess 24 defined in FIG. 6.

Figure 9:
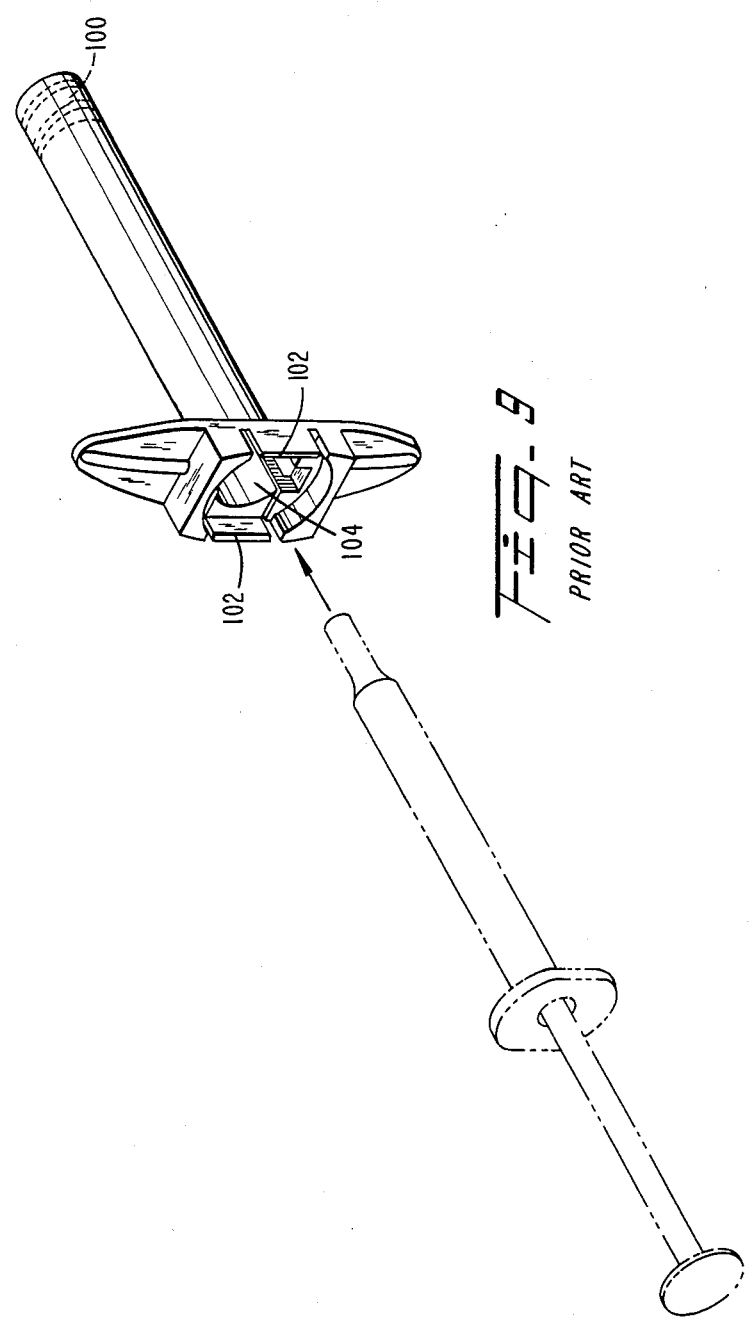
FIG. 9 is a perspective view of a prior art syringe holder.

FIG. 9 is a perspective view of the prior art syringe holder discussed above in the last paragraph under the heading "Discussion of Related Art." This syringe holder includes a luer connection system 100 designed to prevent a needle assembly from being blown off of the syringe. However, the holder is not provided with means for positively preventing axial movement between the holder and a syringe mounted therein, so that the syringe cannot be pulled free of the needle assembly or the syringe holder when viscous material in drawn up into the syringe. Rather, this prior art syringe holder is provided with means 102 to provide a snap-fit between a flange portion of the syringe barrel and the open end portion 104 of the syringe holder. Such a snap-fit arrangement is not capable of positively preventing axial movement between the syringe holder and the syringe, because the syringe may be pulled free of the syringe holder relatively easily by merely applying a retraction force to the syringe sufficient to overcome the retaining forces of the snap-fit arrangement.

In another embodiment of the invention, and as can be seen in FIG. 1, two lugs 13 and 14 are placed near the frontal end of the semicircular channel. These lugs are used to further secure the syringe in the channel once it has been placed in that position.

As will be seen from the above description of the preferred embodiments of the invention, the syringe holder of the invention provides a universal type holder suitable for use with syringes where securing of both the needle assembly and the syringe is required. In preferred embodiments, the holder will be constructed of a plastic material such as a rigid grade of LEXAN ™. As will be seen, the syringe holder provides a positive lock by which the needle assembly is secured to the syringe and will prevent a viscous product from dislodging the needle assembly from the syringe during use. Further, the syringe is secured to the holder in a manner such that the syringe is not pulled free of the needle assembly or the holder when the plunger rod of the syringe is moved backward to draw material into the barrel of the syringe. The holder is adapted for use with any syringe which dose not have a locking device for the needle. The holder is particularly useful in the dispensing of viscous products from small diameter bore syringes wherein a large force is generated by the viscous product during use.

The invention has been described herein with reference to certain preferred embodiments. However, as obvious variations thereon will become apparent to those skilled in the art, the invention is not to be considered as limited thereto.

What is claimed is:

1. A holder for securing a syringe to a needle assembly, comprising a body for receiving said syringe having frontal and distal ends, said frontal end having means for securing an ear portion of said syringe to prevent axial movement between said syringe and said body, said distal end having an opening with a luer lok mechanism through which the forward portion of said syringe is disposed whereby the luer lock secures the forward portion of the syringe; wherein the body comprises an elongate semicircular channel adapted to receive a syringe, a circular distal end, and a frontal member attached to the frontal end of the semicircular channel; said circular distal end forming a closed barrel along the distal end of the body; said frontal member including a pair of flanges, said flanges spaced slightly away from the end of the semicircular channel and supported by a pair of supports with a recess defined between the flanges and channel by the width of the support, said recess accepting a flange of the syringe, and both flange and support defining a U-shaped area through which a head of said syringe can be placed.

2. The holder of claim 1 wherein the semicircular channel has two opposite lugs with the bottom of each lug attached to the channel, said lugs being attached at a point near the frontal end of the channel and adapted to further secure the syringe to the holder.

3. The holder of claim 1, wherein the circular distal end contains a threaded locking mechanism.

4. The holder of claim 3 wherein the threaded locking mechanism is adapted to receive a needle assembly.

5. In combination, a syringe and a holder for connecting the syringe with a needle assembly, comprising a body for receiving said syringe and having frontal and distal ends, said frontal end having means for securing an ear portion of said syringe to prevent axial movement between said syringe and said body, said distal end having an opening with a luer lok mechanism through which the forward portion of said syringe is disposed whereby the luer lok secures the forward portion of the syringe; wherein the holder body comprises an elongate semicircular channel adapted to receive a syringe, a circular distal end, and a frontal member attached to the frontal end of the semicircular channel; said circular distal end forming a closed barrel along the distal end of the body; said frontal member including a pair of flanges, said flanges spaced slightly away from the end of the semicircular channel and supported by a pair of supports, with a recess defined between the flanges and channel by the width of the supprts, said recess accepting a flange of the syringe, and both flange and support defining a U-shaped area through which a head of said syringe can be placed.

6. The combination of claim 5 wherein the semicircular channel has two opposite lugs with the bottom of each lug attached to the channel, said lugs being attached at a point near the frontal end of the channel and adapted to further secure the syringe to the holder.

7. The device of claim 6, wherein the circular distal end contains a threaded locking mechanism.

8. The combination of claim 7 wherein the threaded locking mechanism is adapted to receive a needle assembly.

9. The combination of claim 5 wherein the syringe comprises a barrel having a tapered distal end, a plunger, a piston, and an ear portion, said syringe being readily insertable into the body and held in position by the luer lock, the lugs, and the seating of the ear portion in the recess of the frontal member.

* * * * *